United States Patent
Becker et al.

(10) Patent No.: US 8,834,395 B2
(45) Date of Patent: Sep. 16, 2014

(54) WOUND DRESSING FOR FINGER/PENIS AND METHOD/SYSTEM OF DELIVERY

(71) Applicants: Jamye Lynn Becker, Oswego, NY (US); Felix Takor Oben, Fulton, NY (US)

(72) Inventors: Jamye Lynn Becker, Oswego, NY (US); Felix Takor Oben, Fulton, NY (US)

( * ) Notice: Subject to any disclaimer, the term of this patent is extended or adjusted under 35 U.S.C. 154(b) by 80 days.

(21) Appl. No.: 13/692,433

(22) Filed: Dec. 3, 2012

(65) Prior Publication Data

US 2013/0144201 A1    Jun. 6, 2013

Related U.S. Application Data

(60) Provisional application No. 61/566,061, filed on Dec. 2, 2011.

(51) Int. Cl.
| | | |
|---|---|---|
| *A61F 5/00* | (2006.01) | |
| *A61F 13/00* | (2006.01) | |
| *A61F 15/00* | (2006.01) | |
| *A61F 13/10* | (2006.01) | |

(52) U.S. Cl.
CPC ......... *A61F 13/00085* (2013.01); *A61F 15/005* (2013.01); *A61F 13/105* (2013.01)
USPC ................... 602/22; 602/20; 602/41; 602/42; 602/60

(58) Field of Classification Search
CPC ....... A61F 5/05875; A61F 5/48; A61F 13/00; A61F 13/02; A61F 13/04; A61F 13/061; A61F 13/14; A61F 13/0203
USPC .......... 602/60–66, 41–49, 22, 30, 5; 2/21–22; D24/143, 148, 189; 604/205
See application file for complete search history.

(56) References Cited

U.S. PATENT DOCUMENTS

| | | | | | |
|---|---|---|---|---|---|
| 1,231,194 | A | * | 6/1917 | Prince | 602/58 |
| 2,646,796 | A | * | 7/1953 | Scholl | 602/60 |
| 2,844,146 | A | * | 7/1958 | Perdue | 602/1 |
| 2,851,034 | A | * | 9/1958 | Hanington | 602/1 |
| 2,856,921 | A | * | 10/1958 | Stoller | 602/1 |
| 3,358,682 | A | * | 12/1967 | Preston | 602/1 |
| 3,941,125 | A | * | 3/1976 | Drake | 206/441 |
| 4,576,699 | A | * | 3/1986 | Sato et al. | 204/192.26 |
| 4,655,223 | A | * | 4/1987 | Kim | 606/148 |
| D296,361 | S | * | 6/1988 | Gerich et al. | D24/143 |
| D335,023 | S | * | 4/1993 | Hutcheson | D2/612 |
| 5,722,575 | A | * | 3/1998 | Smith | 224/217 |
| 5,989,567 | A | * | 11/1999 | Dolisi | 424/400 |
| 6,186,969 | B1 | * | 2/2001 | Bell et al. | 602/64 |
| 6,307,118 | B1 | * | 10/2001 | Reich | 602/42 |
| 6,580,011 | B1 | * | 6/2003 | Jennings-Spring | 602/41 |
| 6,790,192 | B2 | * | 9/2004 | Robinson | 602/21 |
| 7,043,762 | B2 | * | 5/2006 | Greenhalgh | 2/16 |
| 7,249,385 | B2 | * | 7/2007 | Schukraft | 2/21 |
| 7,645,252 | B2 | * | 1/2010 | Jennings-Spring | 602/63 |

(Continued)

*Primary Examiner* — Kim M Lewis
(74) *Attorney, Agent, or Firm* — Hiscock & Barclay, LLP

(57) ABSTRACT

A system for delivering a medical dressing onto an appendage, such as a finger or penis, of a patient includes a medical dressing defined by a flexible tubular sleeve that is configured to elastically expand radially, and a delivery device including a pair of pivotable spreader arms attached to a handle portion. The spreader arms of the delivery device are configured for insertion within the sleeve to enable radial expansion from a first diameter to a larger second diameter and positioning of the medical dressing onto the desired anatomical area.

13 Claims, 3 Drawing Sheets

(56) References Cited

U.S. PATENT DOCUMENTS

| | | | |
|---|---|---|---|
| D625,008 S * | 10/2010 | Boedeker | D24/143 |
| D654,587 S * | 2/2012 | Bacher | D24/133 |
| 8,211,044 B2 * | 7/2012 | Liebowitz | 602/22 |
| 8,250,677 B2 * | 8/2012 | Nicolosi et al. | 2/403 |
| 8,353,886 B2 * | 1/2013 | Bester et al. | 604/347 |
| 8,679,048 B2 * | 3/2014 | Sundstrom et al. | 604/9 |
| 2006/0069334 A1 * | 3/2006 | Moskowitz | 602/5 |
| 2007/0021700 A1 * | 1/2007 | Liebowitz | 602/22 |
| 2008/0195009 A1 * | 8/2008 | Satkowiak | 602/3 |
| 2009/0306569 A1 * | 12/2009 | Cook | 602/43 |
| 2009/0317454 A1 * | 12/2009 | Jennings-Spring | 424/449 |
| 2010/0147908 A1 * | 6/2010 | Skerman | 223/111 |

\* cited by examiner

WOUND DRESSING FOR FINGER/PENIS AND METHOD/SYSTEM OF DELIVERY

CROSS REFERENCE TO RELATED APPLICATION

This application claims priority under applicable sections of 35 U.S.C. §119 and 37 CFR §1.53 to U.S. Application Ser. No. 61/566,061, filed Dec. 2, 2011 and entitled: Wound Dressing for Finger/Penis and Method of Use, the entire contents of which is herein incorporated by reference.

TECHNICAL FIELD

This application generally relates to the field of medicine and more specifically to a medical dressing and related method of use for dressing or housing a finger or penis following a surgical procedure, including a system for application of the medical dressing.

BACKGROUND

Medical dressings are typically applied to a wound site or area, for example, following a surgical procedure. Among the types of dressings that can be applied are those to the finger or penis of a patient for example following a circumcision, but typically these types of dressings require wrapping or otherwise securing the dressing to the affected area. To date, these dressings and procedures for applying same are time consuming and often quite inefficient and ineffective.

Certain versions have been developed that are provided a sleeve-type section that is fitted over an appendage, such as the finger or penis of a subject following the surgical procedure. However and due to swelling and other variations in sizing, there can be a tendency for the dressing to undesirably loosen or fall from the appendage. As a result, there is a general need in the field to provide a more effective and efficient medical dressing as well as a delivery method and system for these areas.

SUMMARY

Therefore and according to a first aspect, a system is provided for delivering a medical dressing to an appendage, such as a finger or penis of a patient, following a surgical procedure. The system includes a medical dressing comprising a flexible tubular sleeve that is configured to radially expand in an elastic manner. A delivery device of the system includes a pair of pivotable spreader arms attached to a handle portion, the spreader arms being configured for insertion within the flexible tubular sleeve to expand the sleeve from a first diameter to a larger second diameter to enable attachment to the appendage of a patient.

In one embodiment, the medical dressing further includes at least one tether or anchor extending from a proximal end of the flexible tubular sleeve. According to at least one version, one end of a flexible sheet portion is attached to the exterior of the tubular sleeve, the flexible sheet portion being configured to be wrapped about the exterior of the sleeve following attachment of same to a patient in order to provide compression to the wound site. Preferably, the flexible sheet portion is made from a tacky material that permits adhesion to itself and the tubular sleeve when wrapped thereabout.

In one version, the handle portion of the delivery device is disposed along the axis defined by the pivoting spreader arms. According to another version, the handle portion is orthogonally disposed relative to the axis defined by the pivoting spreader arms to enable a better line of sight for the user in terms of positioning the dressing relative to the wound site.

According to at least one embodiment, the delivery device biases the spreader arms in an open position such that compressive pressure must be applied onto the handle portion on the part of the user in order to close the pivotable spreader arms.

According to another aspect, there is provided a method for use of a medical dressing and delivery system relative to an appendage, such as a finger or penis of a patient. According to the method, a tubular flexible sleeve is provided following a surgical procedure that is configured such that the sleeve can be elastically expanded in a radial direction. A delivery device is also provided, the delivery device including a pair of pivotable spreader arms attached to a handle portion. The flexible sleeve is configured to receive each of the pivotable spreader arms to enable expanding the tubular sleeve from a first diameter to a second larger diameter for delivery of same to an appendage of a patient.

In one version, the method further includes the step of providing at least one tether or anchor on one end of the tubular sleeve for attaching to a patient after the dressing has been positioned onto the appendage. In a preferred version, four (4) spaced tethers are provided at the end of the tubular sleeve, each of the tethers having free ends that can be secured using tape or other means to the body or hand of the patient.

In an embodiment of the herein described method, one end of a flexible sheet portion is secured to the exterior of the tubular sleeve, in which the flexible sheet portion is configured to circumferentially wrap around the exterior of the tubular sleeve following attachment to a patient to provide additional compression onto the wound site. In a preferred version, the flexible sheet portion is made from a tacky material that allows adhesion to itself and the tubular sleeve when wrapped.

According to at least one embodiment, the tubular sleeve is made from a woven material, the material being sufficiently elastic to permit radial expansion thereof over a range of diameters.

According to yet another aspect, there is provided a method for dressing an injured penis or finger or other appendage following circumcision or other surgical procedure. The method comprises the steps of: providing a substantially tubular elastic sleeve including a distal end and a proximal end. A delivery device is attached to the interior of the sleeve in which the elastic sleeve is opened radially from a first diameter to a second larger diameter using the delivery device. According to a preferred version, the delivery device includes a pair of pivoting spreader arms in which the arms are placed within the flexible sleeve and expand the diameter of the tubular sleeve. The delivery device and opened elastic sleeve can then be placed over the appendage of a patient and the delivery device can be withdrawn from the elastic sleeve, allowing the sleeve to be fitted about the wound site.

In one embodiment, the delivery device includes a handle portion connected to the pair of pivoting spreader arms and in which said delivery device is opened and closed using the handle portion. In a preferred version, the spreader arms are biased in an open position such that compressive pressure must be applied by a user on the handle portion in order to close the spreader arms. In one version, the handle portion is substantially coaxial with the spreader arms of the delivery device. According to another embodiment, the handle portion of the delivery device is substantially orthogonal relative to an axis that is defined by the pivotable spreader arms.

According to one version, the method further includes the step of anchoring the medical dressing to the patient using at least one tether extending from a proximal end of the tubular flexible sleeve.

An advantage using the herein described medical dressing and delivery system is that the herein described dressing covers the shaft of the penis or finger while leaving the surgically excised area open for drainage.

Another advantage realized is that the dressing is elastic in nature and will therefore adjustably stretch in accordance with the shape of the appendage, as needed.

Yet another advantage realized is that the outer flexible sheet portion of the dressing provides additional compression onto the wound. This portion or wrap can preferably be wound about the exterior of the dressing and will adhere to itself without requiring fasteners, tape or other closure means.

Another advantage provided by the herein described system is that the delivery device can be constructed such that the extending spreader arms are biased in an open position. By providing this bias, the arms can only be closed by the user providing inward or compressive pressure using the handle portion. The dressing is engaged by the delivery device by squeezing the handle and then releasing same, expanding the sleeve and enabling the sleeve to be applied to the wound site prior to release of the device. No compressive force is applied to the wound site itself during the application process using the delivery device.

These and other features and advantages will be readily apparent from the following Detailed Description, which should be read in conjunction with the accompanying drawings.

DETAILED DESCRIPTION

The following relates to exemplary embodiments of a medical dressing delivery system as applied to either an injured appendage, such as a finger or penis of a patient following a surgical procedure, such as for example, a circumcision. It is to be understood that the herein described invention is not limited as to the details of its construction or to the arrangement of components set forth in this Detailed Description or as shown in the accompanying drawings. In this respect, the invention is therefore capable of other embodiments and of being practiced and carried out in various ways. In addition, certain terms are used throughout the course of this description in order to provide a suitable frame of reference in regard to the accompanying drawings. These terms, however, are not intended to be overlimiting of the inventive concepts that are described herein, including those of the claims.

Figure 1:
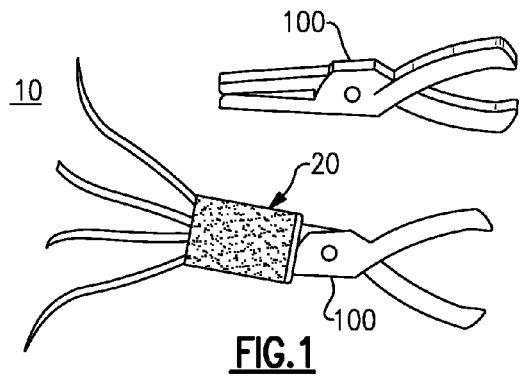
FIG. 1 is a perspective view of a medical dressing and delivery device in accordance with an exemplary embodiment.
Figure 2:
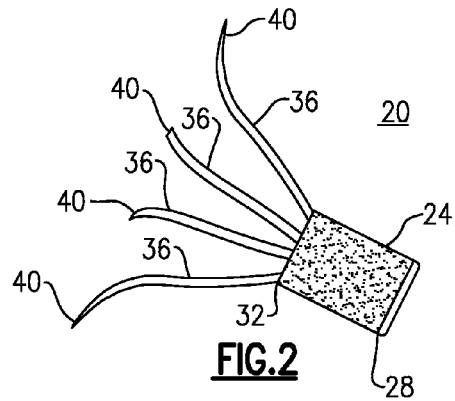
FIG. 2 is a perspective view of an exemplary embodiment of the medical dressing of FIG. 1.

Referring to FIG. 1, there is shown a medical dressing delivery system 10 in accordance with an exemplary embodiment. As shown, the system generally includes a medical dressing 20 and an application or delivery member 100. Referring more specifically to FIGS. 1 and 2, the medical dressing 20 comprises a flexible tubular sleeve 24 having a distal end 28 and an opposing proximal end 32. The sleeve 24 can be defined by an substantially cylindrical member, which is preferably porous and sufficiently flexible to enable radial expansion of the sleeve 24. According to one specific embodiment, the tubular sleeve 24 is constructed from a suitably formed section of stockingette material or from an interwoven structure that includes cotton or other suitable fibrous material that is stitched with a series of elastic threads and in which the sleeve 24 is initially sized to be fitted over the finger or penis of a patient. The overall elasticity of the interwoven material permits the medical dressing 20 to accommodate multiple diameters and also to compensate for swelling effects developing following surgery. A set of tethers 36 or anchors are stitched or otherwise attached to a proximal end 32 of the tubular sleeve 24, each of the tethers 36 extending radially outward from the sleeve 24 and permitting attachment at free ends 40 thereof to portions of a patient, as discussed herein.

The tethers 36 are string-like sections, such as sutures, having an appropriate length (e.g., several inches) that are secured, such as by stitching or other securing means to the proximal end 32 of the tubular sleeve 24. The free ends 40 of each tether 36 can be extended away from the sleeve 24 and secured or anchored to the body or hand. Though not shown, these anchors 36 can be held in place by at least one tape strip, an adhesive or other suitable temporary attachment mechanism.

Figure 3:
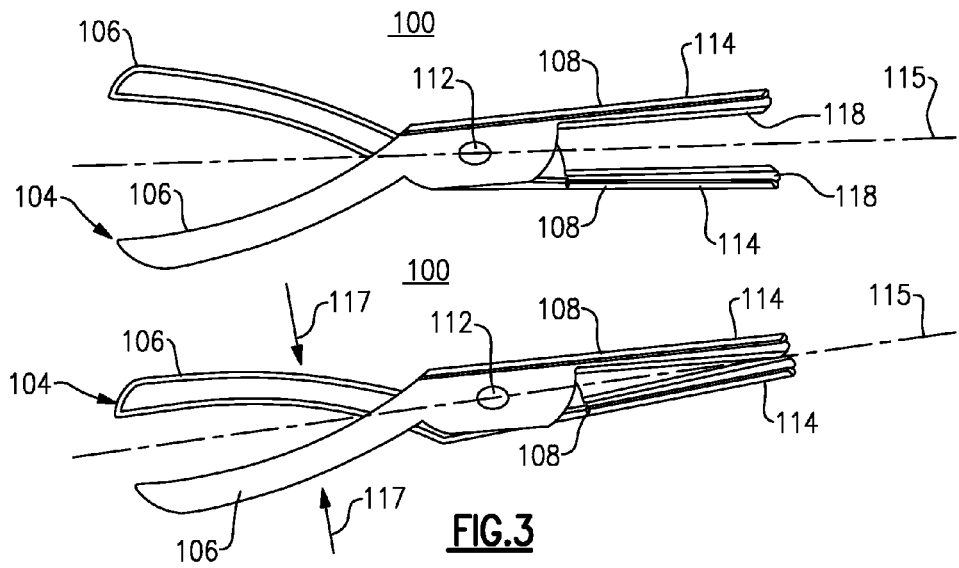
FIG. 3 is a perspective view of the delivery device depicted in FIG. 1.

Referring to FIGS. 1 and 3, the medical dressing delivery system 10 further includes the delivery device 100, which according to this exemplary embodiment is defined by a handle portion 104 provided at one end and a pair of spreader arms 108 at an opposing end of the device. The spreader arms 108 are pivotally attached to the handle portion 104 by means of an intermediate pivot 112, such as, for example, a pin. The handle portion 104 according to this version includes a corresponding pair of spaced handle pieces 106 that are also pivotably attached by means of the intermediate pivot 112. The spreader arms 108 are individually defined by respective elongate sections 114, each having planar distal surfaces 118 that are configured to fit within the confines of the tubular sleeve 100 and in which the handle portion 104, when engaged by the user, enables the spreader arms 108 to move about the intermediate pivot 112. According to this exemplary version, a spring (not shown) provides a biasing force such that the handle pieces 106 of the handle portion 104 and the corresponding spreader arms 108 are biased to an open position. Moving the handle pieces 106 inwardly toward the center axis 115 of the delivery member 100 per arrows 117 acts against the biasing force and causes the spreader arms 108 to close, which facilitates loading of the medical dressing 10 and prevent inadvertent compression of the wound site by the pivoting spreader arms 108. The handle pieces 106 will therefore only have to be compressed in order to load the dressing 10. In this exemplary version, the handle portion 104 of the delivery member 100 extends substantially coaxially with the pivoting spreader arms 108. According to an alternative version, depicted in FIG. 6, a delivery member 160 includes a handle portion 164 that is orthogonally disposed relative to the axis along which a set of pivoting spreader arms 168 are positioned. The foregoing delivery device design provides the user with a better unobstructed line of sight while delivering the medical dressing 20 in this version onto the anatomical target 184 of interest (i.e., finger or penis).

Figure 4:
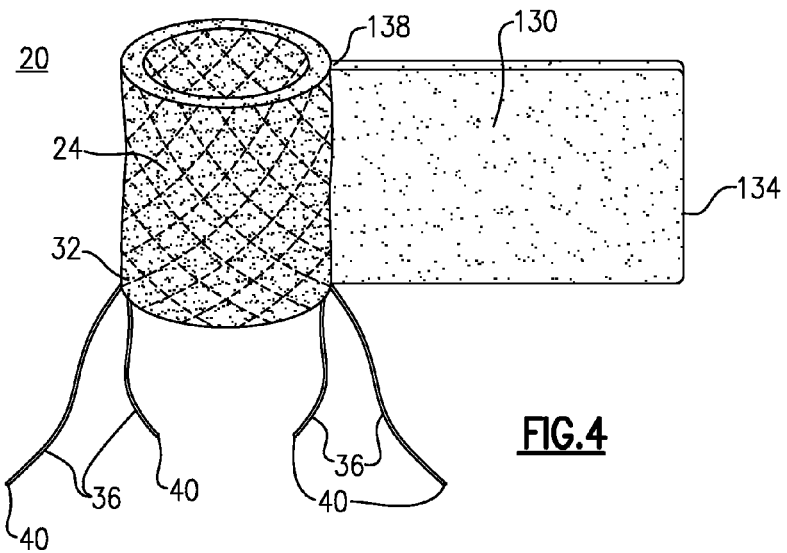
FIG. 4 is an end perspective view of the medical dressing in accordance with another exemplary embodiment.

A medical dressing made in accordance with another exemplary embodiment is shown in FIG. 4. For purposes of clarity, common parts will be labeled with the same reference numerals. This medical dressing 20 is also defined by an elastic tubular sleeve 24 that is further defined by an interwoven porous structure that includes a plurality of tethers or anchors 36 at a proximal end 32. In addition, the tubular sleeve 24 also includes a flexible sheet portion 130 that is stitched or otherwise secured at one end 138 to the exterior of the tubular sleeve 24 along the length thereof. In a preferred version, the flexible sheet portion 130 is made from a tacky fabric that adheres to itself when wrapped circumferentially about the exterior of the sleeve 24.

Figure 5:
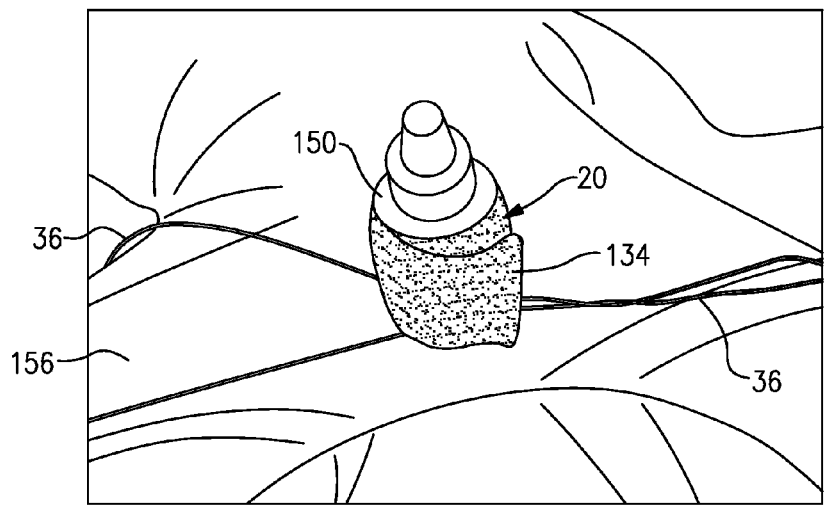
FIG. 5 is a perspective view of the medical dressing of FIG. 4 as attached to a mock anatomical area and secured to a subject.

The sleeve 24 as applied to a mock anatomical target is depicted in FIG. 5. In this view, a bottle is utilized to simulate in this instance the penis of a small child or infant wherein the dressing 20 is placed in overlaying relation such that the proximal end 32 is placed at the base of the penis (or finger or other appendage) and the tethers 36 extend outwardly therefrom for attachment/securement to the legs, abdomen, hand or other adjacent portion of the subject.

Figure 6:
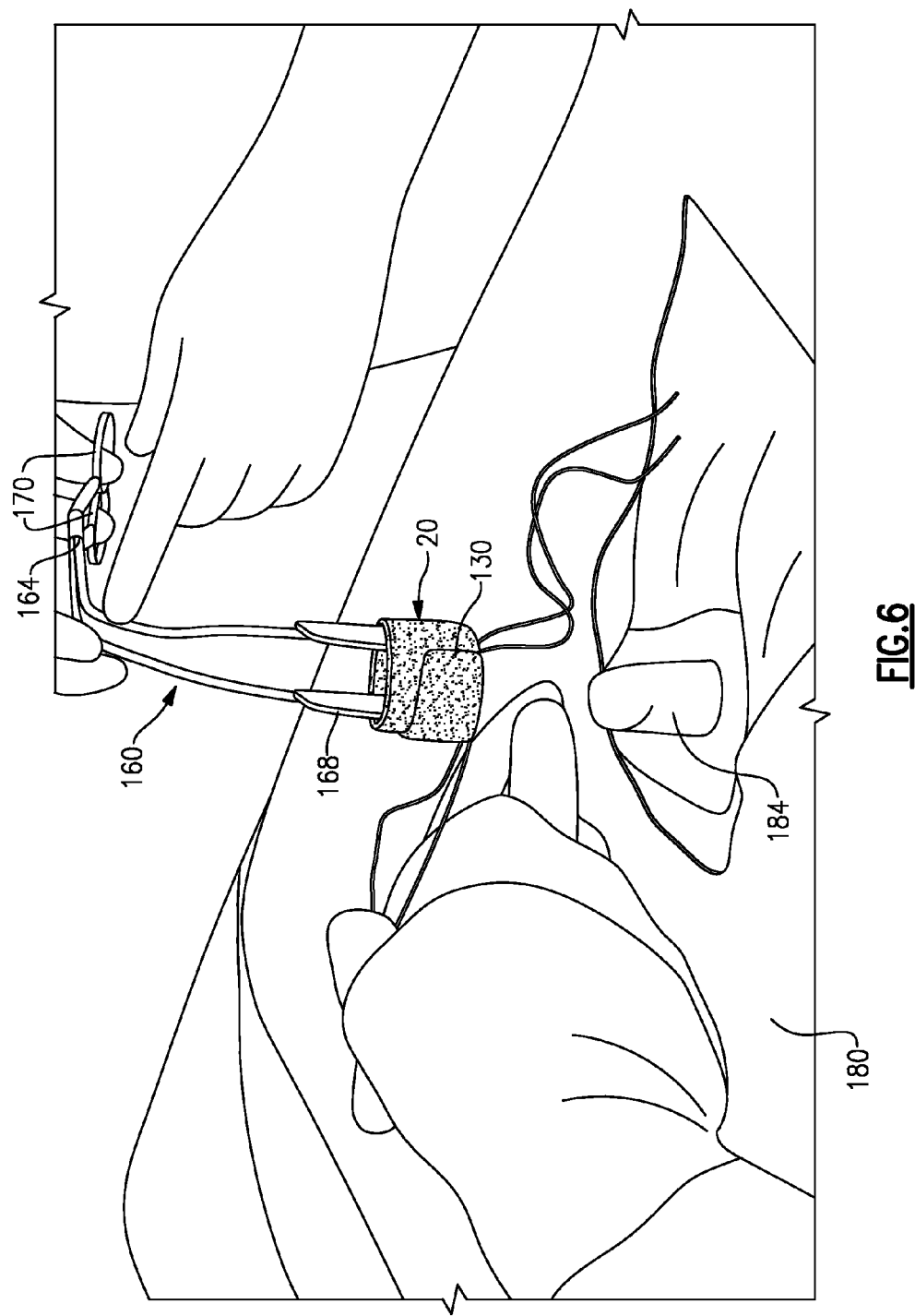
FIG. 6 depicts a delivery device in accordance with another exemplary embodiment in use with a tubular dressing relative to a subject.

The medical dressing delivery system 100 is shown in operation in FIG. 6 using the medical dressing 20 described and shown in FIG. 4. As in the preceding, the same reference numerals are used herein for the sake of clarity. In this exemplary version, the delivery device 160 is initially engaged with the handle pieces 170 and pivoting spreader arms 168 each being initially biased in an open position. In terms of the delivery itself, the handle pieces 170 of the delivery device 160 are squeezed or compressed inwardly by the user in order to initially enable the pivotal spreader arms 168 to access the interior of the tubular sleeve 24 with the arms entering the sleeve 24 from the distal end 28, FIG. 2, and the spreader arms 168 extending significantly into the tubular sleeve 24 itself. Once the medical dressing 20 has been engaged by the spreader arms 168, the inward compressive force on the handle portions 170 is relieved and the biasing force provided by the delivery device 160 causes the arms to revert to their original biased and open position. As a result, the sleeve 24 due to its elastic nature, is caused to expand from its initial diameter to a larger second diameter. This radial expansion then enables the tubular sleeve 24 and the delivery device 160 to be placed over the wound site 184 (i.e., penis) of the patient 180, undergoing a circumcision or other surgical procedure. Because the handle portion 164 is off-axis relative to the pivoting spreader arms 168 of the delivery device 160, the user has an improved line of sight relative to the wound site. Once positioned over the anatomical area of interest, the dressing 20 is slidingly removed from the delivery device 160, which is removed from the patient and in which the size (diameter) of the tubular sleeve 24 accommodates the shaft of the penis with the proximal end 32 being positioned at the base of the shaft of the penis. The flexible sheet portion 130 can then be optionally wrapped about the exterior of the medical dressing 24 to provide additional compression on the wound site and the free ends 40 of the tethers 36 can be attached to the torso of the patient as only partially shown, for example, in FIG. 5.

PARTS LIST FOR FIGS. 1-6

10 medical dressing delivery system
20 medical dressing
24 flexible tubular sleeve
28 distal end, sleeve
32 proximal end, sleeve
36 tethers or anchors
40 free ends, tethers
100 application or delivery member
104 handle portion
106 handle pieces
108 pivoting spreader arms
112 pivot, intermediate
114 elongate sections
115 center axis, delivery device
117 arrows
118 planar distal surfaces
130 flexible sheet portion
134 extending end, sheet portion
138 secured end, sheet portion
150 simulated wound site
156 body
160 application or delivery member
164 handle portion
168 pivoting spreader arms
170 handle pieces or sections
180 patient
184 wound site It will be readily apparent that other variations and modifications are possible within the intended inventive ambits described herein and in accordance with the following claims. For example, the dressing and delivery system can also be used for wound sites involving other appendages, such as the ears and toes, in addition to those discussed herein.

The invention claimed is:

1. A system for delivering a tubular medical dressing relative to an appendage including a finger or penis of a patient following a surgical procedure, said system comprising:
   a medical dressing comprising a flexible tubular sleeve, said flexible tubular sleeve being configured to elastically expand radially, a flexible wrap portion having an end secured along the entire length of said flexible tubular sleeve, and at least one anchor extending from a proximal end of said flexible tubular sleeve, each said at least one anchor extending radially outwardly from the flexible tubular sleeve for permitting attachment at free ends thereof to portions of the appendage; and
   a delivery device including a pair of pivotable spreader arms attached to a handle portion, said delivery device being configured for insertion within said flexible tubular sleeve to expand said sleeve from a first diameter to a larger second diameter to enable attachment to the appendage of a patient wherein the handle portion of the delivery device is orthogonally disposed relative to the pivotable spreader arms.

2. A system as recited in claim 1, wherein said flexible wrap portion is made from a tacky material that permits adhesion to itself and said flexible tubular sleeve when wrapped thereabout.

3. A system as recited in claim 1, wherein said pivotable spreader arms are biased in an open position, requiring actuation by said handle portion in order to effectuate closure of said spreader arms.

4. A method for use of a medical dressing and dressing delivery system, said method comprising the steps of:
   providing a tubular flexible sleeve following a surgical procedure, said tubular flexible sleeve being configured to permit elastic expansion in a radial direction, said tubular flexible sleeve comprising a flexible wrap portion having an end secured along the entire length of said tubular flexible sleeve, and at least one tether extending from a proximal end of said tubular flexible sleeve, each said at least one tether extending radially outwardly from said tubular flexible sleeve for permitting attachment at free ends thereof to portions of an appendage;

providing a delivery device, said delivery device including a pair of pivotable spreader arms attached to a handle portion, said handle portion being orthogonally disposed relative to the pair of pivotable spreader arms, said tubular flexible tubular sleeve being further configured to receive said pair of pivotable spreader arms for expanding said tubular flexible sleeve for delivery of same to a patient; and placing the tubular flexible sleeve on the appendage of a user.

5. A method as recited in claim 4, wherein said delivery device is configured for delivering said medical dressing to at least one of an appendage of a patient, including a finger or penis.

6. A method as recited in claim 4, wherein said flexible wrap portion is configured to circumferentially wrap around an exterior of said tubular flexible sleeve following attachment to a patient to provide additional compression onto a wound site.

7. A method as recited in claim 6, wherein said flexible wrap portion is made from a material that enables adhesion to itself when wrapped.

8. A method as recited in claim 4, including the step of providing a plurality of spaced tethers at the end of said tubular flexible sleeve, each of said tethers including means for anchoring to a patient.

9. A method as recited in claim 4, wherein said tubular flexible sleeve is made from a woven material.

10. A method for dressing an appendage including a penis or finger of a patient following circumcision or other surgical procedure, said method comprising the steps of:

providing a substantially tubular elastic sleeve, said sleeve including a distal end and a proximal end, a flexible wrap portion having an end secured along the entire length of said substantially tubular elastic sleeve, and at least one anchor extending from the proximal end of said substantially tubular elastic sleeve, each said at least one anchor extending radially outwardly from the substantially tubular elastic sleeve for permitting attachment at free ends thereof to portions of the appendage;

attaching a delivery device to an interior of said tubular elastic sleeve, said delivery device comprising a handle portion connected to a pair of pivoting spreader arms, said handle portion being substantially orthogonal to the pair of pivoting spreader arms;

radially opening said tubular elastic sleeve from a first diameter to a second larger diameter using said delivery device;

placing said delivery device and said tubular elastic sleeve over the appendage of the patient; and withdrawing said delivery device from said tubular elastic sleeve, allowing said tubular elastic sleeve to be fitted about the appendage.

11. A method as recited in claim 10, wherein said delivery device is opened and closed using said handle portion.

12. A method as recited in claim 10, wherein the spreader arms are biasedly maintained in an open position.

13. A method as recited in claim 10, further including the step of securing said tubular elastic sleeve using at least one tether extending from a proximal end of said tubular elastic sleeve.

* * * * *